United States Patent

Hutchings et al.

[11] Patent Number: 5,723,629
[45] Date of Patent: Mar. 3, 1998

[54] THIOPHENE SYNTHESIS

[75] Inventors: Graham John Hutchings, Osmotherley; Richard William Joyner, Birkenhead; Barry William Luke Southward, Widnes; Russel Andrew Stewart, Wolverhampton; Lance Svend Fuller, Trussell, all of Great Britain

[73] Assignee: Shell Research Limited, Great Britain

[21] Appl. No.: 669,017

[22] Filed: Jun. 24, 1996

[30] Foreign Application Priority Data

Jun. 28, 1995 [EP] European Pat. Off. ............ 95304563

[51] Int. Cl.$^6$ .................. C07D 333/10; B01J 23/20
[52] U.S. Cl. .................. 549/85; 502/316
[58] Field of Search ................. 549/85; 502/316

[56] References Cited

U.S. PATENT DOCUMENTS 2,558,508  6/1951  Appleby et al. ............... 549/85
3,822,289  7/1974  Clark et al. ................... 549/85
4,143,052  3/1979  Barrault et al. ............... 549/85

Primary Examiner—S. Mark Clardy
Assistant Examiner—Mary C. Cebulak

[57] ABSTRACT

A method of preparing a thiophene comprises reacting an organic compound containing a chain of at least 4 C atoms linked by single or double bonds with a source of sulphur in the vapour phase, in the presence of a jarosite-type catalyst, having the composition $$M(Fe_{0.8-1}Cr_{0.2-0})(OH)_6X_n$$

wherein M is $NH_4$ or an alkali metal; and $X_n$ represents one or more suitable anions.

20 Claims, No Drawings

THIOPHENE SYNTHESIS

FIELD OF THE INVENTION

This invention relates to a method for preparing thiophenes.

BACKGROUND OF THE INVENTION

Various syntheses of thiophene and its homologues are known. For example, GB-A-1345203 describes the reaction of an organic compound containing a consecutive chain of at least 4 carbon atoms linked by single or double bonds, and optionally carrying substituents, with carbon disulphide, in the vapour phase, and in the presence of a catalyst. The catalyst may be an oxidation, dehydration or dehydration catalyst, e.g. chromia-alumina, molybdenum oxide or manganese oxide, and is preferably promoted by alkali or alkaline earth metal.

Grose et al. in "Preparation of Catalysts", ed. Delmon et al, Elsevia Scientific Publishing Company, Amsterdam (1976) pages 51–61, describe hydrocarbon conversion catalysts derived from synthetic alunite-type and jarosite-type crystal structures. Jarosite-derived catalysts based on iron oxide showed activity comparable to that of Girdler G-64, a commercial dehydrogenation catalyst.

SUMMARY OF THE INVENTION

The present invention is based on the discovery that the above thiophene synthesis can be catalysed by compounds of the structure

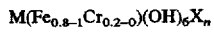

$$M(Fe_{0.8-1}Cr_{0.2-0})(OH)_6X_n$$

wherein M is $NH_4$ or an alkali metal, and $X_n$ represents one or more suitable anions; in particular jarosite itself, i.e. $Na[Fe_3(SO_4)_2(OH)_6]$. These catalyst act at relatively low temperatures e.g. about 340° C., and their catalytic effect can be enhanced partial substitution of the Fe content by Cr (III).

DETAILED DESCRIPTION

The catalyst initially has the jarosite mineral structure; see Dana et al, The System of Mineralogy 7th Ed. Vol. 2, 555, J. Wiley & Sons, NY (1951). During the reaction the crystal structure of the catalyst is modified to give a mixed structural framework. Analysis of such a catalyst's morphology during this phase has shown this framework to comprise various proportions of jarosite/bracewellite/goethite crystalline types; the catalyst activity may be assisted by such modification.

While the range of Cr substitution may be up to 20%, it is preferably 1–15%, more preferably 2–10% and most preferably 2–7%, e.g. about 5%. If the levels of Cr exceed the indicated amounts, further major structural change may eventually occur. This may lead to an amorphous state, typical of supported metal oxides, giving reduced catalytic specific activity.

As in jarosite itself, $X_n$ is preferably $(SO_4)_2$. It may, however, be an isomorph thereof. Such a catalyst may be prepared by refluxing Fe/Al(III) sulphate (+Cr/dopant) solution, while adding MOH, e.g. sodium or ammonium hydroxide, at pH 4 at 85°–95° C. for 20–24 hours.

Attempts to support the catalyst used in the present invention have provided little advantage. However, it is generally advantageous to use a promoter, such as an alkali or alkaline earth metal, which may be added to the catalyst after the formation of the catalyst has otherwise been completed. Preferred alkali metals are potassium and sodium. Examples of alkaline earth metals are calcium and barium.

The addition of potassium or other alkali or alkaline earth metal can be made to a preformed catalyst by adding potassium carbonate or some other alkali compound. The amount of alkali or alkaline earth metal compound present on the catalyst can be, for example, from 4–20% by weight, calculated as potassium carbonate.

The starting materials that may be used in the method of the invention are organic compounds containing a consecutive chain of at least 4 carbon atoms linked by single or double bonds. Any of the carbon atoms of the chain may be unsubstituted or they may be individually substituted by a functional group such as hydroxyl, oxygen, alkyl, aralkyl or aryl. Optionally, two adjacent carbon atoms in the chain may form part of an aromatic or heterocyclic ring system. Examples therefore include alkanes, olefins, ketones, aldehydes and alcohols, and the alkanes may be substituted by, for example, aryl.

The choice of starting material controls the thiophene that is obtained. Thus, a starting material containing solely 4 carbon atoms in a straight chain will produce thiophene while a starting material containing more than 4 carbon atoms will produce a substituted thiophene.

The starting compound may be an alcohol, and the alcohol can be a dihydric alcohol or it can be unsaturated. It may be substituted by one or more substituents individually selected from hydrogen, alkyl, aryl, aralkyl or heterocyclic substituents. A suitable heterocyclic substituent is pyridyl. A typical unsubstituted starting alcohol is but-2-enol and a typical dihydric alcohol is 1,4-butanediol.

By way of example, if the starting material is n-butanol, the product is thiophene. Further, a pentanol will yield a methylthiophene, 1-hexanol yields 2-ethyl-thiophene and 1-heptanol yields 2-propylthiophene. If that starting alcohol is substituted at the 2- and/or 3- positions, the thiophene will be substituted in the 3- and/or 4-positions. For example, 2-ethylbutan-1-ol yields 3-ethylthiophene.

Other starting materials that may be used include olefins. They may have more than one unsaturated position and may be substituted as indicated for alcohols. Suitable olefins include butadiene, isoprene and butenes such as 2-methylbut-1-ene.

A variety of ketones or aldehydes can be used as starting material. Broadly any ketone or aldehyde having a carbon skeleton substituted as defined above for alcohols could be used. Examples are butyraldehyde, crotonaldehyde, butenal and methyl isobutyl ketone. Similarly, a wide variety of alkanes can be used, and again any alkane having a carbon skeleton of 4 consecutive carbon atoms, but which can also be substituted, can be used.

Particularly useful starting materials include those comprising a benzene ring substituted by a straight chain of 2 or more carbon atoms since these can result in the formation of benzothiophenes. For example, reaction of ethyl benzene in the process of the invention results in the formation of benzo(b) thiophene; sec-butylbenzene will give 3-phenylthiophene.

A range of sulphur-containing feedstock materials can be used. Examples include carbon disulphide, hydrogen sulphide, carbonyl sulphide and sulphur. Carbon disulphide is preferred.

The temperature of the reaction is suitably between 275° and 450° C., preferably 340° C.–400° C., since at lower temperatures conversion of the starting compound and yield of desired thiophene drops sharply, and there is no particular merit in operating above 450° C. The fact that good conversion can be achieved at 340° to 400° C. is an important advantage of this invention.

Provided there is sufficient carbon disulphide present it is easily possible to achieve substantially complete conversion of the starting compound, for example 99% or more. This is especially desirable when the starting material is an alcohol, since thiophene and its homologues tend to form azeotropes with the alcohols that may be used, with the result that separation of the thiophene from admixture with the alcohol could be difficult.

The mole ratio of carbon disulphide to the starting material may be from 4:1 to 0.1:1, preferably from 2:1 to 1:1. Thus, an excess over the equimolar amount of carbon disulphide can be used.

The contact time with the catalyst is usually between 0.1 and 20 seconds. Preferably, it is 4 to 8 seconds, with the best results often being achieved at about 5 seconds. Higher values tend to reduce the yield of thiophene, while maintaining high conversion, while lower values tend to reduce both the conversion and the amount of product obtained.

The reaction is normally conducted at atmospheric pressure but higher or lower pressures may be used.

It is known that catalysts for this reaction lose activity due to the accumulation of coke. In the event of this occurring, the catalyst may be regenerated by heating in air or with steam/air mixtures.

The following Examples illustrate the invention.

EXAMPLE 1-8

3-Methylthiophene was produced by the reaction of equimolar amounts of 2-methylbutanol and carbon disulphide under a flow of nitrogen and over a range of temperatures and catalyst systems. The catalysts of these examples were 1 ml quantities from catalyst preparations resulting in the formation of a synthetic jarosite or jarosite equivalents, in which a proportion of the iron (FeIII) was replaced by varying levels of chromium (CrIII) as detailed in the procedure above. Standard microreactor conditions are detailed in table 1.

TABLE 1

| Catalyst volume ml | 1.0 |
|---|---|
| Reaction feed | 1:1 by vol. Alcohol: CS$_2$ |
| LHSV hr$^{-1}$ | 1.0 |
| Temperature °C. | 300–500 |

Table 2 indicates the level of chromium substitution for the iron in the catalyst preparations of examples 1-8.

TABLE 2

| Example Number | % Cr Substitution on catalyst |
|---|---|
| 1 | 1.0 |
| 2 | 2.5 |
| 3 | 5.0 |
| 4 | 10.0 |
| 5 | 15.0 |
| 6 | 25.0 |
| 7 | 50.0 |
| 8 | 100.0 |

In all cases the reaction products were similar with 3-methylthiophene (3MT) and alkene production together with low levels of products from cracking reactions. Catalytic activity was seen to be temperature dependent. The particularly favoured low temperature range (300°–375° C.) activity being enhanced by low levels of Cr on the catalyst, but suppressed by higher Cr levels of substitution. Thus a trend for low temperature activity is noted as follows:

5% > 2.5% > 10% > 1% ~ 0% > 25% > 50% > 100%

Four classes of activity can be envisaged with respect to the level of Cr substitution and temperature:

1. Preferred Level, 2% <CR>10%, T<400° C. Catalyst activity was seen to be most efficient in these ranges of Cr loading and temperature, with minimum levels of cracked products.

2. Low Level, Cr<15%, for T>380° C. performance loss was observed with a decrease in 3MT yield and alcohol conversion. However, unlike the unsubstituted catalyst there is no significant increase in cracking.

3. Intermediate Level, 10%<Cr<25%, at T>380° C. the catalyst continued to product 3MT (this yield increasing with temperature). However, the yield of alkene decreased whilst the yields of thiophene and cracked products increased with temperature—a result typical of supported metal oxide catalysts.

4. High Level, Cr>25%. These catalyst displayed no low temperature activity indicating a loss of the active site. Even at % >380° C. any activity displayed was poor.

EXAMPLE 9

The procedure of examples 1-8 was repeated using the 2.5% Cr loaded catalyst promoted with 7.5% potassium carbonate, K$_2$CO$_3$. Results indicate yield of 3MT and conversion figures of 60.9% and 86.0%/80.2% at 340° C. and 400° C. respectively.

Compare example 2 for the yield of 3MT/conversion: 50.7%/30.2% and 74.8%/55.5% respectively.

It can be seen that the effect of the promoter is twofold. Firstly it increases the yield of 3MT by approximately 10/15%, secondly and more significantly the maximum activity of the catalyst is maintained over a temperature range 60° C. wide, between 340°–400° C. Throughout this temperature range the product yield is maintained at least above 60% rather than reaching a maximum and then decaying.

EXAMPLE 10

The procedure of example 9 was repeated, but using the 5% Cr loaded jarosite catalyst promoted with 7.5% K$_2$CO$_3$. The results giving yield of 3MT and conversion gave: 63.2%/84.4% and 62.1%/85.6% at 340° and 380° respectively. Compare results from example 3 using unpromoted 5% Cr loaded jarosite, when the 3MT yield/conversion figures were: 56.2%/75.2% and 34.8%/58.1% at 340° C. and 380° C. respectively.

The yield of 3MT is again seen to be above 60%, significantly above the yield obtained from the unpromoted catalyst. Catalyst activity is also seen as a plateau over a wide temperature range with yield of 3MT remaining above 60% and conversion above 80% over a 400° C. wide range of temperatures.

EXAMPLES 11 and 12

Current thiophene synthesis catalysts are based on supported metal oxide systems, typically a suitable catalyst is G41P supplied by Girdler S. A. A comparison of the performance of the new catalyst system based on mineral structures with G41P was made in these two examples.

Reaction performances for this study had to be based on equal surface areas for the comparison to be meaningful. Hence a larger volume of the 5% Cr jarosite catalyst was used in the microreactor.

Comparative surface areas:

| | |
|---|---|
| 5% Cr Jarosite | SA = 103 m² g⁻¹ |
| G41P | SA = 125 m² g⁻¹ |

The results are given for the reaction of 2-methylbutanol to 3-methylthiopohene over the temperature range 300°–500° C. In the novel lower temperature range yields of 3MT over the 5% Cr jarosite catalyst was more efficient: 73% at 92% conversion, at 340° C. At such time the G41P catalyst gave a yield of 3MT of 50% at 73% conversion.

G41P catalysis of this reaction was however, much more efficient in the temperature range 425°–475° C. The advantages of the new chromium substituted jarosite catalysts are thereby confirmed when operated over the 340°–400° C. temperature range.

What is claimed is:

1. A method of preparing a thiophene, which comprises reacting an organic compound containing a chain of at least 4 C atoms linked by single or double bonds with a source of sulfur in the vapor phase, in the presence of a catalyst comprising the composition $$M(Fe_{0.8-1}Cr_{0.2-0})(OH)_6X_n$$

wherein M is $NH_4$ or an alkali metal; and $X_n$ represents one or more suitable anions.

2. A method according to claim 1, wherein $X_n$ is $(SO_4)_2$.
3. A method according to claim 1, wherein M is Na or K.
4. A method according to claim 2, wherein M is Na or K.
5. A method according to claim 1, wherein the Fe:Cr ratio is $$Fe_{0.9-0.98}Cr_{0.1-0.02}.$$

6. A method according to claim 2, wherein the Fe:Cr ratio is $$Fe_{0.9-0.98}Cr_{0.1-0.02}.$$

7. A method according to claim 3, wherein the Fe:Cr ratio is $$Fe_{0.9-0.98}Cr_{0.1-0.02}.$$

8. A method according to claim 4, wherein the Fe:Cr ratio is $$Fe_{0.9-0.98}Cr_{0.1-0.02}.$$

9. A method according to claim 1, wherein said catalyst is promoted by Na or K.
10. A method according to claim 2, wherein said catalyst is promoted by Na or K.
11. A method according to claim 4, wherein said catalyst is promoted by Na or K.
12. A method according to claim 8, wherein said catalyst is promoted by Na or K.
13. A method according to claim 1, which is conducted at 275° to 450° C.
14. A method according to claim 2, which is conducted at 275° to 450° C.
15. A method according to claim 4, which is conducted at 275° to 450° C.
16. A method according to claim 8, which is conducted at 275° to 450° C.
17. A method according to claim 12, which is conducted at 275° to 450° C.
18. A method according to claim 1, wherein the source of sulphur is carbon disulphide.
19. A method according to claim 2, wherein the source of sulphur is carbon disulphide.
20. A method according to claim 4, wherein the source of sulphur is carbon disulphide.

* * * * *